United States Patent
Hara et al.

(10) Patent No.: US 6,777,208 B2
(45) Date of Patent: Aug. 17, 2004

(54) METHOD FOR PRODUCING 2'-DEOXYRIBONUCLEOSIDE

(75) Inventors: Seiichi Hara, Kawasaki (JP); Naoto Tonouchi, Kawasaki (JP); Kenzo Yokozeki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/983,657

(22) Filed: Oct. 25, 2001

(65) Prior Publication Data

US 2002/0164720 A1 Nov. 7, 2002

(30) Foreign Application Priority Data

Oct. 25, 2000 (JP) ......................................... 2000-325521

(51) Int. Cl.$^7$ ........................... C12P 19/38; C12N 1/20; C12N 15/63; C07H 21/04
(52) U.S. Cl. ................. 435/87; 435/252.3; 435/252.33; 435/320.1; 435/88; 536/23.2
(58) Field of Search ......................... 435/252.3, 252.33, 435/87, 320.1, 88; 536/23.2

(56) References Cited

FOREIGN PATENT DOCUMENTS

| JP | 58-63393 | 4/1983 |
|---|---|---|
| JP | 64-60396 | 3/1989 |
| JP | 1-104190 | 4/1989 |
| JP | 2-39894 | 2/1990 |
| JP | 11-137290 | 5/1999 |

OTHER PUBLICATIONS

NCBI Blast search using Acc#gi/26251274 deoD Nucleoside phosphorylase from *E. coli*.*

Koellner et al Crystal structure of the ternary complex of *E. coli* purine nuleoside phosphorylase with formycin B, a structural analogue of the substrate inosine, and phosphate (Sulphate) at 2.1 A resolution. J. Mol Biol. Jul. 3, 1998; 280(1): 153–66.*

Metzler Biochemistry: The Chemical Reactions of Living Cells. Academic Press New York, NY. pp. 4 and 44.*

NCBI Blast search, Alignment of the *E. Coli* NrdEF gene products from S. typhimurium, C. ammoniagenes, and L. lactis.*

Ausbel, 1987a Protein Expression In: Current Protocols in Molecular Biology Chapter 16.*

Ausbel, 1987b Mutagenesis of cloned DNA. In: Current Protocols in Molecular Biology Chapter 8.*

Kornberg, 1980a Ribnonucleotide reduction to deoxyribonucleotide. In: DNA Replication. W.H. Freeman and Co, New York p55–60.*

Kornberg, 1980b Salvage pathway of nucleotide synthesis. In: DNA Replication. W.H. Freeman and Co, New York p64–70.*

Schafer, Tauch, Jager, Kalinowski, Thierbach, Puhler. Small mobilizable multi–purpose cloning vectors derived from the *Escherichia coli* plasmids pK18 and pK19: selection of defined deletions in the chromosome of Corynebacterium g. Gene. 1994 145; p 69–73.*

A. Brunella, et al., Journal of Molecular Catalysis B: Enzymatic, vol. 10, pp. 215–222, "Recombinant Lactobacillus Leichmannii Ribonucleosidetriphosphate Reductase as Biocatalyst in the Preparative Synthesis of 2' –Deoxyribonucleoside–5' –Triphosphates", 2000.

* cited by examiner

*Primary Examiner*—Rebecca Prouty
*Assistant Examiner*—S Swope
(74) *Attorney, Agent, or Firm*—Oblon, Spivak, McClelland, Maier & Neustadt, P.C.

(57) ABSTRACT

A 2'-deoxyribonucleoside is produced by culturing a microorganism, which is transformed with a gene encoding a ribonucleotide reductase and in which 2'-deoxyribonucleoside degradation activity is decreased or eliminated by disrupting a gene encoding a purine nucleoside phosphorylase on chromosomal DNA, in a medium in which the microorganism can grow to produce the 2'-deoxyribonucleoside.

6 Claims, 3 Drawing Sheets

_METHOD FOR PRODUCING 2'-DEOXYRIBONUCLEOSIDE_

BACKGROUND OF THE INVENTION

1. Field of the Invention

The present invention relates to a method for producing a 2'-deoxyribonucleosides such as 2'-deoxyguanosine and a microorganism suitably used for the method. 2'-Deoxyribonucleosides are useful as raw materials of drugs, intermediate thereof and so forth.

2. Description of the Related Art

As methods for producing 2'-deoxyribonucleosides, there are known chemical synthesis methods, methods of extracting them from hydrolysates of DNA and biochemical production methods.

As the biochemical methods, there are known methods of producing 2'-deoxyribofuranosylpurine and 2'-deoxyribofuranosylthioguanine (Japanese Patent Laid-open Publication (Kokai) No. 58-63393), 2'-deoxycytidine (Japanese Patent Laid-open Publication No. 01-060396) and 2'-deoxythymidine (Japanese Patent Laid-open Publication No. 01-104190) by using nucleoside phosphorylases of microorganisms.

Further, as methods that utilize microorganisms, there have been disclosed a method of producing 2'-deoxyadenosine from deoxyribose-1-phosphate or a salt thereof and adenine, adenosine or 5'-adenylic acid, a method of producing 2'-deoxyadenosine from 2'-deoxyuridine or thymidine and adenine, adenosine or 5'-adenylic acid in the presence of inorganic phosphoric acid or a salt thereof, a method of producing 2'-deoxyguanosine from 2'-deoxyribose-1-phosphate or a salt thereof and guanine, guanosine or 5'-guanylic acid, and a method of producing 2'-deoxyguanosine from 2'-deoxyuridine or thymidine and guanine, guanosine or 5'-guanylic acid in the presence of inorganic phosphoric acid or a salt thereof (Japanese Patent Laid-open Publication No. 11-137290).

There has also been reported a method of producing a 2'-deoxyribonucleoside-5'-phosphate from a ribonucleotide as a raw material in the presence of a reducing agent such as dithiothreitol by using a recombinant type enzyme, which is obtained by isolating a gene for ribonucleoside triphosphate reductase of a _Lactobacillus bacterium_ and expressing this gene in _Escherichia coli_ (Brunella, A. et al., _Journal of Molecular Catalysis B: Enzymatic_, 10, 215–222 (2000)).

Furthermore, there have been reported a method of producing thymine or thymidine by culture utilizing viable microbial cells (Japanese Patent Laid-open Publication No. 2-39894).

DISCLOSURE OF THE INVENTION

Objects of the present invention is to provide a method for efficiently producing a 2'-deoxyribonucleoside such as 2'-deoxyguanosine by using a microorganism and a microorganism used for the method.

The inventors of the present invention assiduously studied in order to achieve the aforementioned objects. As a result, they found that a deoxyribonucleoside could be efficiently produced from a carbon source, ribonucleoside or base by using a microorganism having increased ribonucleotide reductase activity and decreased deoxyribonucleoside degradation activity, and thus accomplished the present invention.

That is, the present invention provides the followings.

(1) A method for producing a 2'-deoxyribonucleoside, which comprises culturing a microorganism, which is transformed with a gene encoding a ribonucleotide reductase and in which 2'-deoxyribonucleoside degradation activity is decreased or eliminated, in a medium in which the microorganism can grow to produce the 2'-deoxyribonucleoside.

(2) The method for producing a 2'-deoxyribonucleoside according to (1), wherein a ribonucleoside or base corresponding to the 2'-deoxyribonucleoside is added to the medium.

(3) The method for producing a 2'-deoxyribonucleoside according to (1) or (2), wherein the 2'-deoxyribonucleoside is 2'-deoxyguanosine.

(4) The method for producing a 2'-deoxyribonucleoside according to any one of (1) to (3), wherein the 2'-deoxyribonucleoside degradation activity of the microorganism is decreased or eliminated by disrupting a gene encoding a purine nucleoside phosphorylase on chromosomal DNA.

(5) The method for producing a 2'-deoxyribonucleoside according to any one of (1) to (4), wherein the ribonucleotide reductase does not suffer from feedback inhibition by a deoxyribonucleotide.

(6) The method for producing a 2'-deoxyribonucleoside according to any one of (1) to (5), wherein the ribonucleotide reductase is a ribonucleoside diphosphate reductase.

(7) The method for producing a 2'-deoxyribonucleoside according to any one of (1) to (6), wherein the microorganism is a bacterium belonging to the genus Escherichia.

(8) A microorganism, which is transformed with a gene encoding a ribonucleotide reductase, in which a gene encoding a purine nucleoside phosphorylase on chromosomal DNA is disrupted, and which has an ability to produce a 2'-deoxyribonucleoside.

(9) The microorganism according to (8), wherein the ribonucleotide reductase is a ribonucleoside diphosphate reductase.

According to the present invention, a 2'-deoxyribonucleoside such as 2'-deoxyguanosine can be produced by using a microorganism.

Hereafter, the present invention will be explained in detail.

The microorganism used for the present invention is a microorganism which is transformed with a gene encoding a ribonucleotide reductase, in which 2'-deoxyribonucleoside degradation activity is decreased or eliminated, and which has an ability to produce a 2'-deoxyribonucleoside from a carbon source, ribonucleoside or base.

The microorganism of the present invention will be explained hereafter.

In the present invention, preferred microorganisms include microorganisms having an ability to supply reducing power. The term "ability to supply reducing power" means an ability to supply a reducing substance (for example, reducing type of glutaredoxin) in an amount sufficient for advance of the reaction for reducing a ribonucleoside diphosphate to convert it into a 2'-deoxyribonucleoside diphosphate, which is catalyzed by a ribonucleotide reductase. As such microorganisms having ability to supply reducing power referred to in the present invention, bacteria belonging to the genus Escherichia can be mentioned, for example. Examples of such bacteria belonging to the genus Escherichia include _Escherichia coli_.

The microorganism of the present invention can be obtained by decreasing or eliminating the 2'-deoxyribonucleoside degradation activity of a microorganism and then transforming it with a ribonucleotide reductase gene. The microorganism of the present invention can also be obtained by transforming a microorganism with a ribonucleotide reductase gene and then decreasing or eliminating the 2'-deoxyribonucleoside degradation activity of the transformant strain.

In order to transform a microorganism with a ribonucleotide reductase gene, specifically, a gene fragment encoding a ribonucleotide reductase can be ligated to a vector functioning in the microorganism, preferably a multi-copy type vector to produce a recombinant DNA, and it can be introduced into the microorganism to transform it.

The source of the ribonucleotide reductase gene is not particularly limited so long as it is a microorganism containing a ribonucleotide reductase. For example, there can be mentioned *Escherlchia coli, Corynebacterium ammoniagenes, Saccharomyces cerevisae, Lactobacillus leichmannii* and so forth.

In the present invention, the ribonucleotide reductase is preferably one that does not suffer from feedback inhibition by a deoxyribonucleotide. Examples of a ribonucleotide reductase include ribonucleoside diphosphate reductases and ribonucleoside triphosphate reductases.

In *Escherichia coli*, there are known three types of ribonucleoside diphosphate reductases, NrdAB, NrdDG, and NrdEF, and it has been reported that NrdAB and NrdDG suffer from feedback inhibition by a deoxyribonucleotide such as 2'-dATP, whereas NrdEF does not suffer from such feedback inhibition (*J. Biol. Chem.*, 271 (43), 26582–26587 (1996)). Therefore, among the aforementioned three types of the enzymes, NrdEF is preferred.

A nucleotide sequence of a gene encoding NrdEF of *Escherichia coli* (nrdEF) has been reported (GenBank accession number D90891), and the nrdEF gene can be obtained by synthesizing primers based on the nucleotide sequence and performing polymerase chain reaction (PCR, see White, T. J. et al., *Trends Genet.*, 5, 185 (1989)) using the primers and chromosomal DNA of a bacterium belonging to the genus Escherichia, for example, the *Escherichia coli* W3110 strain, as a template. Examples of the primers include oligonucleotides having the nucleotide sequences shown in SEQ ID NOS: 1 and 2.

The vector used for the introduction of ribonucleotide reductase gene into a host microorganism may be one that can replicate in the host microorganism, and specific examples thereof include plasmid vectors such as pBR322, pTWV228, pMW119, pUC19 and pUC18.

In order to prepare a recombinant DNA by ligating a ribonucleotide reductase gene and a vector that functions in a bacterium belonging to the genus Escherichia, the vector can be digested with restriction enzymes suitable to the termini of the ribonucleotide reductase gene fragment and then the both can be ligated. The ligation is usually performed by using a ligase such as T4 DNA ligase.

The recombinant DNA prepared as described above can be introduced into a host microorganism by, for example, a method reported for *Escherichia coli* such as the method of D. A. Morrison (*Methods in Enzymology*, 68, 326 (1979)) or a method in which recipient cells are treated with calcium chloride to increase permeability for DNA (Mandel, M. and Higa, A., *J. Mol. Biol.*, 53, 159 (1970)). Besides the use of plasmid vector, the recombinant DNA can also be incorporated into genome of a host by a method utilizing transduction, transposon (Berg, D. E. and Berg, C. M., *Bio/Technol.*, 1, 417 (1983)), Mu phage (Japanese Patent Laid-open Publication No. 2-109985) or homologous recombination (Experiments in Molecular Genetics, Cold Spring Harbor Lab. (1972)).

As a promoter for the expression of the ribonucleotide reductase gene, when a promoter specific for a ribonucleotide reductase gene functions in host cells, this promoter can be used. Alternatively, it is also possible to ligate a foreign promoter to a DNA encoding a ribonucleotide reductase so as to obtain its expression under the control of the promoter. As such a promoter, when a bacterium belonging to the genus Escherichia is used as the host, lac promoter, trp promoter, trc promoter, tac promoter, $P_R$ promoter and $P_L$ promoter of lambda phage, tet promoter, amyE promoter, spac promoter and so forth can be mentioned. Further, it is also possible to use an expression vector containing a promoter like pUC18 or pUC19, and insert a DNA fragment encoding a ribonucleotide reductase into the vector so that the fragment can be expressed under the control of the promoter.

When a microorganism contains a gene encoding a ribonucleotide reductase, the ribonucleotide reductase activity can be increased by replacing an expression regulatory sequence such as a promoter for the gene with a stronger one (see Japanese Patent Laid-open No. 1-215280). For example, all of the aforementioned promoters functioning in bacteria belonging to the genus Escherichia have been known as strong promoters.

Methods for preparation of chromosomal DNA, PCR, preparation of plasmid DNA, digestion and ligation of DNA, transformation, design and synthesis of oligonucleotides used as primers and so forth may be usual ones well known to those skilled in the art. Such methods are described in, for example, Sambrook, J., Fritsch, E. F., and Maniatis, T., "Molecular Cloning: A Laboratory Manual, Second Edition", Cold Spring Harbor Laboratory Press (1989) and so forth.

A method for decreasing or eliminating the 2'-deoxyribonucleoside degradation activity of microorganism will be explained hereafter. In order to reduce or eliminate the 2'-deoxyribonucleoside degradation activity, for example, a mutation can be introduced into a gene encoding a purine nucleoside phosphorylase or the gene can be disrupted so that the intracellular purine nucleoside phosphorylase activity should be decreased or eliminated. In *Escherichia coli*, the deoD gene codes for purine nucleoside phosphorylase. A deoD gene-disrupted strain can be obtained by, for example, incorporating a DNA fragment containing a part of deoD gene into chromosomal DNA of the microorganism by homologous recombination with the deoD gene on the chromosome.

Specifically, the deoD gene on chromosome can be disrupted by transforming a microorganism such as *Escherichia coli* with DNA containing the deoD gene modified by partial deletion so as not to produce a purine nucleoside phosphorylase that functions normally (deletion type deoD gene) to cause recombination between the deletion type deoD gene and the deoD gene on the chromosome. Such gene disruption based on homologous recombination has already been established, and the gene disruption can also be attained by methods utilizing a linear DNA or a plasmid containing a temperature sensitive replication origin and so forth. A method utilizing a plasmid containing a temperature sensitive replication origin will be explained hereafter.

There is prepared a DNA containing the deoD gene modified so that an internal sequence of the deoD gene should be deleted and it should not produce a purine nucleoside phosphorylase that functions normally (deletion type of deoD gene). The deoD gene on the host chromosome can be replaced with this deletion type of deoD gene as follows. That is, a recombinant DNA is prepared by inserting a temperature sensitive replication origin, the mutant deoD gene and a marker gene for resistance to a drug such as ampicillin, and a microorganism is transformed with this recombinant DNA. The resultant transformant strain is cultured at a temperature at which the temperature sensitive replication origin does not function, and then the transformant strain can be cultured in a medium containing the drug to select a transformant strain in which the recombinant DNA is introduced into the chromosomal DNA.

In such a strain in which the recombinant DNA is incorporated into the chromosome as described above, the mutant deoD gene is recombined with the deoD gene originally present on the chromosome, and two of fusion genes of the chromosomal deoD gene and the deletion type of deoD gene are inserted into the chromosome so that the other portions of the recombinant DNA (vector segment, temperature sensitive replication origin and drug resistance marker) should be present between two of the fusion genes. Therefore, in this state, the transformant expresses the normal deoD, because the normal deoD gene is dominant.

Then, in order to leave only the deletion type of deoD gene on the chromosomal DNA, one copy of the deoD gene is eliminated with the vector segment (including the temperature sensitive replication origin and the drug resistance marker) from the chromosomal DNA by recombination of two of the deoD genes. In this case, the normal deoD gene may be left on the chromosome DNA and the deletion type deoD gene may be excised from the chromosomal DNA, or to the contrary, the deletion type of deoD gene may be left on the chromosomal DNA and the normal deoD gene may be excised from the chromosomal DNA. In the both cases, the excised DNA may be retained in the cell as a plasmid when the cell was cultured at a temperature at which the temperature sensitive replication origin can function. Subsequently, the cell is cultured at a temperature at which the temperature sensitive replication origin cannot function. In this case, when the deletion type of deoD gene is left on the chromosomal DNA, the plasmid containing the normal deoD gene is eliminated from the cell. Therefore, the purine nucleoside phosphorylase is decreased or eliminated. On the other hand, when the normal deoD gene is left on the chromosomal DNA, the purine nucleoside phosphorylase is exhibited. Thus, a desired strain can be obtained by allowing each recombinant strain to grow in, for example, a medium containing inosine, and then analyzing the culture broth by thin layer chromatography to select a clone that does not degrade the inosine into hypoxanthine. Furthermore, it is preferable to amplify a fragment containing deoD by PCR from chromosomal DNA of a candidate strain and confirm disruption of the deoD gene by analysis utilizing restriction enzymes or the like.

A 2'-deoxyribonucleoside can be produced by culturing a microorganism obtained as described above, which is transformed with a gene encoding a ribonucleotide reductase and in which 2'-deoxyribonucleoside degradation activity is decreased or eliminated in a medium to produce a 2'-deoxyribonucleoside and collecting the deoxyribonucleoside. The microorganism to be used may consist of one kind of microorganism or an arbitrary mixture of two or more kinds of microorganisms.

Examples of the 2'-deoxyribonucleoside produced by the method of the present invention include 2'-deoxyguanosine, 2'-deoxyadenosine, thymidine, 2'-deoxyuridine, 2'-deoxyinosine and so forth. In the present invention, 2'-deoxyguanosine is preferred among these.

As the aforementioned substrate or its precursor, there can be mentioned a ribonucleoside or nucleobase corresponding to a target 2'-deoxyribonucleoside. Examples of the ribonucleoside include guanosine, adenosine, ribothymidine, uridine, inosine and so forth, and examples of the nucleobase include guanine, adenine, thymine, uracil, hypoxanthine and so forth. For example, when the target 2'-deoxyribonucleoside is 2'-deoxyguanosine, guanosine or guanine is used as a corresponding ribonucleoside or nucleobase.

The "medium in which a microorganism can grow" used in the present invention may be one in which the microorganism can acquire energy by metabolism. In this respect, there can be used an ordinary medium containing a carbon source, nitrogen source, phosphorus source, sulfur source, inorganic ions and so forth, as well as vitamins and organic nitrogen source as required. There can be suitably used carbohydrates such as glucose, alcohols such as glycerol, organic acids such as acetic acid and so forth as the carbon source; ammonia gas, aqueous ammonia, ammonium salts, nitric acid and salts thereof and so forth as the nitrogen source; inorganic phosphoric acid and salts thereof such as monopotassium phosphate and so forth as the phosphorus source; magnesium sulfate and so forth as the sulfur source; magnesium ions, potassium ions, iron ions, manganese ions and others as the inorganic ions, as required. As a source of organic nutrients, there can be suitably used vitamins, amino acids and yeast extract, peptone, meat extract, corn steep liquor and casein degradation product containing them and so forth. The culture conditions are not also particularly limited, and the culture can be performed, for example, under an aerobic condition at a pH of 5–8 and a temperature of 25–40° C. for about 12 to 72 hours, while pH and temperature are suitably controlled.

Further, the substrate or a precursor thereof may be added to the medium. The substrate may be added to the medium at an early stage of the culture or in the middle of the culture.

The 2'-deoxyribonucleoside produced as described above can be isolated and collected by ordinary methods for isolation and collection such as those utilizing absorptive synthetic resins and others. Further, the 2'-deoxyribonucleoside can be quantified by a method utilizing high performance liquid chromatography.

BEST MODE FOR CARRYING OUT THE INVENTION

Hereafter, the present invention will be explained more specifically with reference to the following examples.

EXAMPLE 1

Cloning of *Escherichia coli* nrdEF Gene

Chromosomal DNA of the *Escherichia coli* W3110 strain was prepared by the method given in Current Protocols in Molecular Biology (John Wiley & Sons). Separately, two kinds of oligonucleotide primers shown as SEQ ID NOS: 1 and 2 were synthesized based on the nucleotide sequence of nrdEF gene in a gene data bank (*E. coil* GenBank, Accession number D90891). These primers had EcoRI and SAlI recognition sites at the 5' ends, respectively.

A DNA fragment of about 3.6 kb was amplified by performing PCR under ordinary conditions by using 100 pmol each of the aforementioned primer DNAs and 1 μg of the aforementioned chromosomal DNA. This DNA fragment was separated and collected by agarose gel electrophoresis, digested with EcoRI and SalI at the both ends and ligated with a plasmid pUC18 (Takara Shuzo) digested with EcoRI and SalI. The *Escherichia coli* JM109 strain was transformed with the ligation product, and a transformant strain containing the nrdEF gene was selected. The plasmid obtained as described above, which contained the nrdEF gene, was designated as pUCnrdEF.

EXAMPLE 2

Production of deoD Gene-disrupted Strain and nrdEF Gene-introduced Strain of *Escherichia coli* W3110

A deoD gene-disrupted strain of the *Escherichia coli* W3110 was produced by the same method as disclosed in European Patent Application EP 1,004,663, which corresponds to International Patent Publication WO99/03988. Specifically, it was produced as follows.

PCR was performed (94° C., 30 sec; 55° C., 1 min; 72° C., 2 min; 30 cycles; Gene Amp PCR System Model 9600 (Perkin-Elmer)) by using the chromosomal DNA of the W3110 strain as a template and 30-mer and 31-mer primers for the both ends, which were produced based on the information retrieved from a gene data bank (*E. coli* Gene Bank) by using "deoD" as a keyword and had the nucleotide sequences of CTCGTCGACGCGGGTCTGGAACTGTTC-GAC (SEQ ID NO: 3) and CTCGCATGCCCGTGCTT-TACCAAAGCGAATC (SEQ ID NO: 4), and the amplified fragment of about 1350 bps containing the deoD structural gene region covering SD-ATG and the translation stop codon was cloned into pCRTMII vector (Invitrogen). This vector contained EcoRI sites as restriction enzyme sites near both ends of the cloning site. Moreover, the primers for PCR were designed to contain SalI site and SphI site, respectively.

Figure 1:
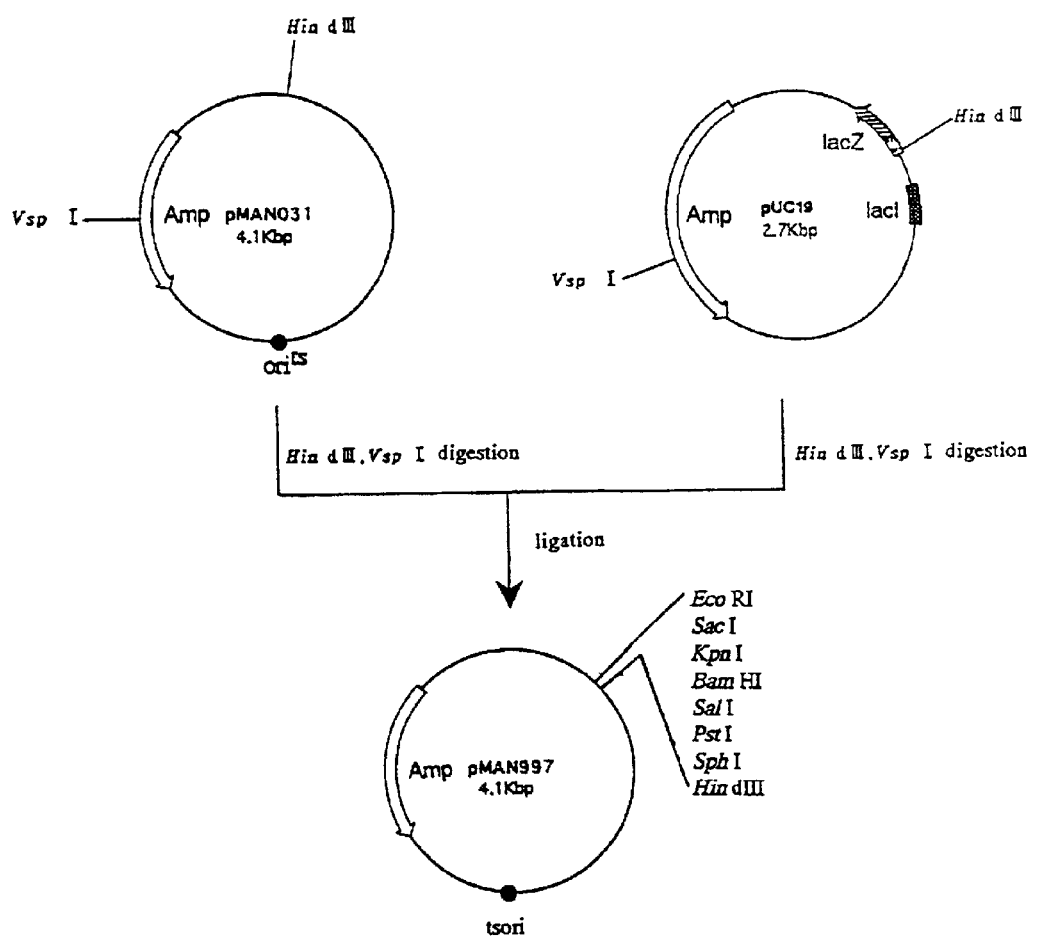
FIG. 1 shows the structure of the vector pMAN997 for homologous recombination, which has a temperature sensitive replication origin.

Since the cloned deoD fragment of about 1350 bps contained one HpaI site at a position of about 680 bps from the 5' end, the plasmid was digested with HpaI, and the digested plasmid and a 10-mer ClaI linker were mixed and subjected to a T4 ligase reaction. As a result, a ClaI site was inserted at the HpaI site. This ligation solution was used to transform *E. coli* HB101 competent cells and transformants grown on an LB agar plate containing 25 μg/ml of ampicillin were obtained. Plasmid DNAs were prepared from 16 clones of the transformants, and among these, a plasmid DNA that was not digested with HpaI, but digested with ClaI was selected (pCRTMIIdeoD' #16). The deoD gene contained in this plasmid DNA would have a frame shift at the HpaI site, and thus it was predicted that the encoded enzyme no longer had its function (FIG. 1).

Then, pCRTMIIdeoD' #16 was digested with EcoRI to prepare a fragment of about 1.35 kbs containing deoD. This fragment was inserted into an EcoRI site of pMAN997, which was a vector for homologous recombination and contained a temperature sensitive replication origin (tsori), to obtain a plasmid pMAN997deoD' #16. The aforementioned pMAN997 was obtained by exchanging VspI-HindIII fragments of pMAN031 (*J. Bacteriol.*, 162, 1196 (1985)) and pUC19 (Takara Shuzo).

The W3110 strain was transformed with the plasmid pMAN997deoD' #16 at 30° C., and the obtained colonies were applied to an LB agar plate containing 25 μg/ml of ampicillin and cultured overnight at 30° C. Then, the cultured cells were applied to an LB agar plate containing 25 μg/ml of ampicillin so that single colonies should be obtained, and colonies grown at 42° C. were obtained. The procedure of obtaining single colonies grown at 42° C. was repeated once again, and clones in which the whole plasmid was incorporated into the chromosome by homologous recombination were selected. It was confirmed that these clones did not contain the plasmid in cytoplasm.

Then, the aforementioned clones were applied to an LB agar plate, cultured overnight at 30° C., then inoculated to LB liquid medium (3 ml/test tube), and cultured at 42° C. for 3 to 4 hours with shaking. This culture was appropriately diluted so that single colonies should be obtained (about $10^{-5}$ to $10^{-6}$), applied to an LB agar plate, and cultured overnight at 42° C. to obtain colonies. From the emerged colonies, 100 colonies were randomly picked up and grown on an LB agar plate and an LB agar plate containing 25 μg/ml of ampicillin, respectively, and ampicillin sensitive clones that grew only on the LB agar plate were selected. The ampicillin sensitive clones were further grown in LB medium added with 1 g/L of inosine. These culture broths were analyzed by thin layer chromatography to select clones that did not degrade inosine into hypoxanthine. Furthermore, a fragment of about 1.35 kbs containing deoD was amplified by PCR from chromosomal DNA of each of the above target clones and it was confirmed that it could be digested with ClaI, but not with HpaI. A clone that satisfied the above requirements was considered as a deoD-deleted strain and the obtained strain was designated as W3110ΔAdeoD.

The W3110ΔdeoD was used as a recipient strain and transformed with the plasmid produced in Example 1 to obtain a strain in which the deoD gene was disrupted and the nrdEF gene was amplified (W3110ΔdeoD/pUCnrdEF).

EXAMPLE 3

Production of 2'-deoxyguanosine by Strain in Which deoD Gene was Disrupted and nrdEF Gene Was Amplified (I)

Figure 2:
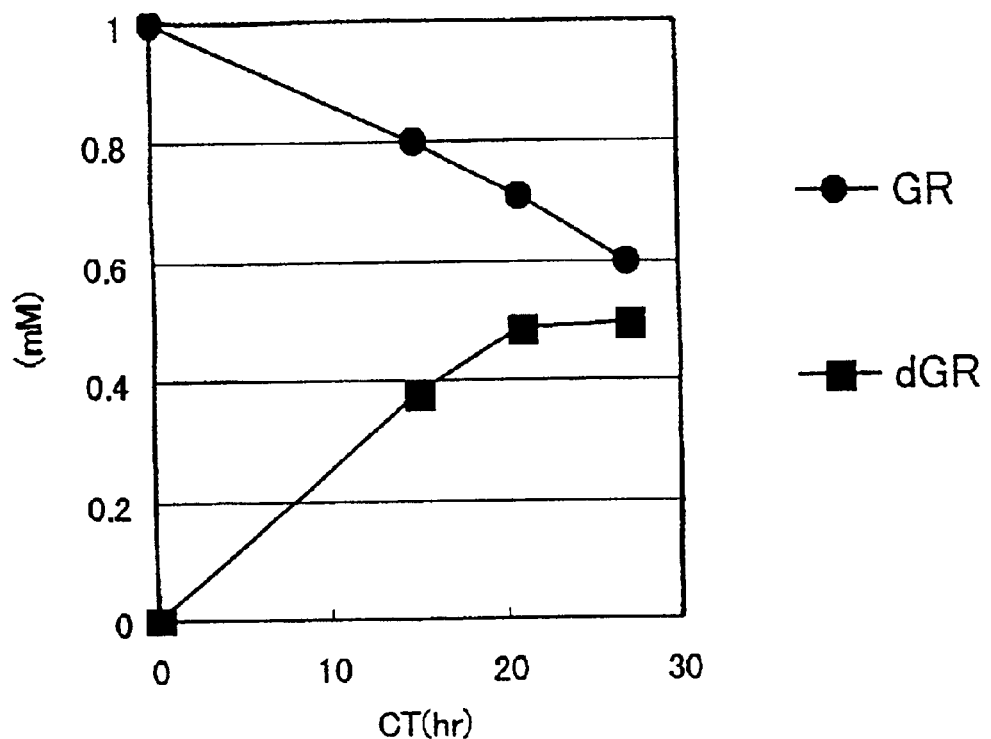
FIG. 2 shows production of 2'-deoxyguanosine from guanosine. GR represents guanosine and dGR represents 2'-deoxyguanosine.

A medium containing 20 g/L of trypton, 10 g/L of yeast extract and 20 g/L of NaCl (pH 7.0) was put into 500 ml-volume Sakaguchi flasks in an amount of 12.5 ml each and sterilized at 120° C. by heating for 20 minutes. To this medium, 12.5 ml of 2 mM guanosine separately sterilized by using a filter and ampicillin separately sterilized by using a filter at a concentration of 100 mg/L were added. The *Escherichia coli* W3110ΔdeoD/pUCnrdEF strain was inoculated into the medium and cultured at 37° C. with shaking. After the cells were removed by centrifugation, 2'-deoxyguanosine produced in the medium was quantified by HPLC. As a result, production of 2'-deoxyguanosine increasing with time was observed as shown in FIG. 2.

EXAMPLE 4

Production of 2'-deoxyguanosine by Strain in Which deoD Gene was Disrupted and nrdEF Gene was Amplified (II)

Figure 3:
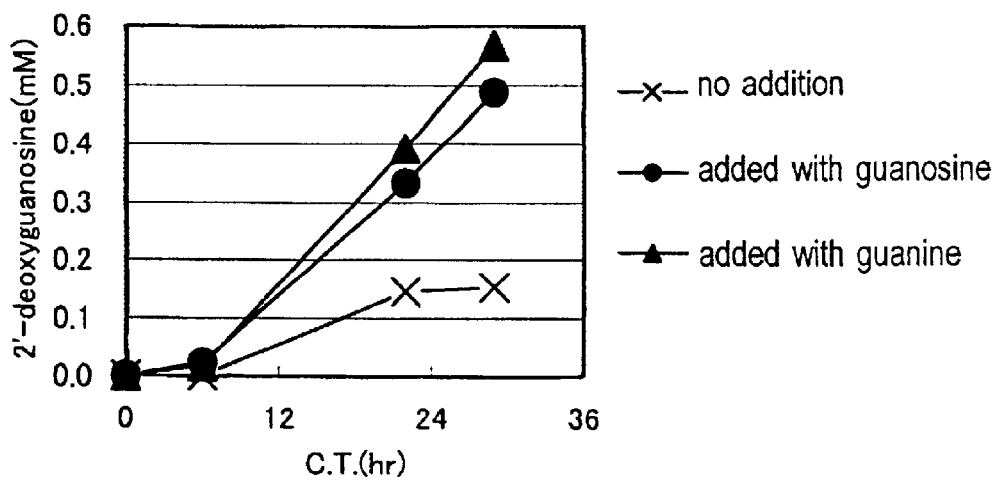
FIG. 3 shows production of 2'-deoxyguanosine in a medium added with guanosine or guanine, or in a non-addition medium.

A sterilized medium having the undermentioned composition was put into 500 ml-volume Sakaguchi flasks in an amount of 20 ml each and added with 0.4 g of $CaCO_3$ separately subjected to dry sterilization and ampicillin separately sterilized by using a filter at a concentration of 100 mg/L. The *Escherichia coil* W3110ΔdeoD/pUCnrdEF strain was inoculated into the medium and cultured at 37° C. with shaking. After the cells were removed by centrifugation, 2'-deoxyguanosine produced in the medium was quantified by HPLC. Further, 1 mM sterilized guanosine addition plot and 10 mM sterilized guanine addition plot were also tested. As a result, 2'-deoxyguanosine was accumulated to a concentration of 0.15 mM for the no addition plot, 0.49 mM for the guanosine addition plot and 0.57 mM for the guanine addition plot. The time courses of 2'-deoxyguanosine accumulation are shown in FIG. 3.

| [Medium composition] | |
|---|---|
| Glucose | 20 g/l |
| $MgSO_4$ | 0.5 g/l |
| $K_2HPO_4$ | 3 g/l |
| $KH_2PO_4$ | 1 g/l |
| $(NH_4)_2SO_4$ | 5 g/l |
| $FeSO_4$ | 10 mg/l |
| $MnSO_4$ | 10 mg/l |

What is claimed is:

1. A method for producing a 2'-deoxyribonucleoside, which comprises culturing a bacterium belonging to the genus Escherichia, which is transformed with a gene encoding a ribonucleotide reductase and in which the 2'-deoxyribonucleoside degradation activity is decreased or eliminated by disrupting a gene encoding a purine nucleoside phosphorylase on chromosomal DNA of the bacterium, in a medium in which the bacterium can grow to produce the 2'-deoxyribonucleoside, wherein the gene encoding a ribonucleotide reductase comprises a sequence which is amplified by PCR using oligonucleotides having sequences of SEQ ID NOs:1 and 2 as primers and the chromosoinal DNA of the bacterium as a template, and wherein the gene encoding a purine nucleoside phosphorylase comprises a sequence which is amplified by PCR using oligonucleotides having sequences of SEQ ID NOs:3 and 4 as primers and the chromosonial DNA of the bacterium as a template.

2. The method for producing a 2'-deoxyribonucleoside according to claim 1, wherein a ribonucleoside, or base corresponding to the 2'-deoxyribonucleoside is added to the medium.

3. The method for producing a 2'-deoxyribonucleoside according to claim 1, wherein the 2'-deoxyribonucleoside is 2'-deoxyguanosine.

4. The method for producing a 2'-deoxyribonucleoside according to claim 1, wherein the ribonucleotide reductase does not suffer from feedback inhibition by a deoxyribonucleoside.

5. The method for producing a 2'-deoxyribonucleoside according to claim 1 wherein the ribonucleotide reductase is a ribonucleoside diphosphate reductase.

6. The method for producing a 2'-deoxyribonucleoside according to claim 1, wherein the bacterium is a bacterium belonging to *Eseherichia coli*.

* * * * *

SEQUENCE LISTING

<160> NUMBER OF SEQ ID NOS: 4

<210> SEQ ID NO 1
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
ccgggaattc cggctggcgc ggtgccacga                    30

<210> SEQ ID NO 2
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
ggcagtcgac gcaacccctg atggaaatg                     29

<210> SEQ ID NO 3
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
ctcgtcgacg cgggtctgga actgttcgac                    30

<210> SEQ ID NO 4
<211> LENGTH: 31
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
ctcgcatgcc cgtgctttac caaagcgaat c                  31